United States Patent [19]

Sherman

[11] Patent Number: 4,551,461

[45] Date of Patent: Nov. 5, 1985

[54] SOFT CONTACT LENS AMBIENT TEMPERATURE DISINFECTANT AND RINSING SOLUTION AND METHOD

[75] Inventor: Guy J. Sherman, Mandeville, La.

[73] Assignee: Sherman Laboratories, Inc., Abita Springs, La.

[21] Appl. No.: 642,088

[22] Filed: Aug. 20, 1984

Related U.S. Application Data

[63] Continuation-in-part of Ser. No. 537,245, Sep. 28, 1983, Pat. No. 4,529,535, which is a continuation-in-part of Ser. No. 384,110, Jun. 1, 1982, abandoned.

[51] Int. Cl.$^4$ .................... A01N 43/54; A61K 31/505
[52] U.S. Cl. .................................... 514/275; 252/106; 252/173; 252/DIG. 14; 422/28
[58] Field of Search ................... 252/106, 173, 174.23, 252/174.24, 542; 424/78, 80, 252, 343, 251; 422/28; 514/275

[56] References Cited

U.S. PATENT DOCUMENTS 3,954,965  5/1976  Boghosian et al. ................... 424/81
4,470,978  9/1984  Stolar ................................. 424/229

OTHER PUBLICATIONS

The Merck Index, An Encyclopedia of Chemicals & Drugs, Merck & Co., N.J., Ninth Ed., 1976, p. 1246.

Primary Examiner—Prince E. Willis
Attorney, Agent, or Firm—Jenner & Block

[57] ABSTRACT

Aqueous compositions for the ambient temperature or cold disinfection of soft contact lenses during non-wearing periods is provided. The composition includes water and a disinfectant composition comprising an effective amount of trimethoprim for killing bacteria, usually between about 0.05% and 4.0% by weight of the total aqueous composition and an effective amount of benzyl alcohol as agent to and adjuvant bactericide, usually between about 0.50% and 5.0% by weight of the total composition and optionally a salt of EDTA. A method is provided for treating the lenses to kill bacteria associated with the lenses.

16 Claims, No Drawings

SOFT CONTACT LENS AMBIENT TEMPERATURE DISINFECTANT AND RINSING SOLUTION AND METHOD

RELATED APPLICATIONS

This application is a continuation-in-part application of U.S. patent application Ser. No. 537,245 filed Sept. 28, 1983, now U.S. Pat. No. 4,529,535 which is a continuation-in-part application of U.S. patent application Ser. No. 384,110 filed June 1, 1982, now abandoned.

BACKGROUND OF THE INVENTION

Just as there are marked differences in the structure and composition of hard and soft contact lenses, there are also marked differences in the maintenance and care or treatment of the various types of hard, semi-hard and soft lenses. While patient care and treatment of hard contact and uncomplicated or conventional contact lenses is relatively simple and uncomplicated, the proper care and treatment of the newer soft and hydrophilic lenses has proved to be more complex and time consuming.

The primary difference between the conventional hard contact lens and the more complex soft lenses is the marked increase in the polar or water attracting centers of the hydrophilic gel material. It is this property of the hydrophilic gel lens that gives the soft lens its own unique physical properties and clinical behavior. This polar or water attracting center of the gel material is represented in the hydroxyethyl methacrylate bond as a hydroxyl group (-OH) which attracts and holds large amounts of water. It is this high water content held in the expanded matrix of the hydrophilic gel lens which leads to the special difficulties in and disinfecting or asepticising the soft hydrophilic lens. The hydrophilic nature of soft contact lenses makes the lenses vulnerable to bacterial contamination. While studies have demonstrated that bacteria cannot penetrate the actual intramolecular pores of the hydrophilic lens, except in defective lenses, the bacteria have an affinity for the protein and tear deposits on the surfaces of the lens matrix. In particular, the tears and fluids absorbed in the soft lenses serve as excellent bacterial culture media. If defects or nicks occur in the lens either during manufacture or subsequent patient wear, bacteria may find a haven to grow and be sheltered from superficial lens cleaning and disinfection.

Potentially harmful fungi also provide a possible danger to the soft contact lens. Fungi, like bacteria, can thrive in tear secretions or deposits and penetrate the lens material directly if enzymatic degradation of the lens material has taken place.

Other problems can accrue from incorrect and careless handling of the soft lenses by the patient himself. Many potential contaminants and lens deposits can be transferred from unwashed fingers to the surface of the soft lens. These include oily deposits from the skin, sweat, skin lotions and creams, mascara, detergents, lipstick and even nicotine. Controlled studies have demonstrated that bacterial contaminants occur in 43% of the makeup used by women, and fungal contaminants in 12%. Attempts to effect sterilization of the lenses by boiling, for example, can be cumbersome in addition to causing permanent damage to the lenses if done improperly. If the patient has used impure water for storage and rinsing of the lenses, undesirable deposits such as calcium, iron and insoluble divalent and trivalent metallic salts as well as other chemical deposits can collect on the lens surfaces.

Therefore, a need has arisen for an effective composition to counteract and mitigate the above described effects of improper hygiene and lens handling as well as to provide optimum disinfection and storage of the soft lens between lens wearing periods. In addition, the active ingredients of an effective contact lens solution should preferably: (1) disinfect clean soft lenses within a period of four to six hours and produce D values of a 90% kill rate of microorganisms, selected fungal and yeast organisms, and viral agents such as herpes simplex; (2) not be easily inactivated by small amounts of proteins, lipids or other tear and extraneous components and deposits; (3) not bind to protein or other lens surface deposits from the eye; and (4) not react with or absorb to the soft lens material or matrix. For example, several antiseptic agents which meet the above requirement for rapid and effective kill of a broad range of microorganisms have proved to be unsuitable for use in soft lens treatment solutions, in that these agents are incompatible with the soft lens material or bind with protein deposits on the surfaces of the lens matrix. Other antiseptic agents are unacceptable for use in soft lens solutions since they are concentrated by the lens material, to the extent that they cause discomfort and potential damage to the corneal surface of the wearer's eyes. Benzalkonium chloride is one such antiseptic agent which meets the requirements for the effective and rapid killing of microorganisms but is unacceptable because it binds with many types of soft lens material and also binds with protein deposits on the lens surface.

One type of cold disinfecting solution for soft contact lenses uses chlorhexidene. However, chlorhexidene is absorbed by the soft contact lens material and gradually eluded into the eye often causing excessive burning, irritation and red eye, in addition to discoloring soft lenses, which can prevent the patient from wearing the lenses.

Therefore, a need has arisn for a highly effective cold storage and disinfecting solution and method for the overnight or interim disinfection and storage of soft, silicone and silicone co-polymer contact lenses which meet the aforesaid requirements.

SUMMARY OF THE INVENTION

In accordance with the present invention, an aqueous storage and disinfecting solution containing trimethoprim and benzyl alcohol for the ambient temperature or cold storage and disinfection of soft, silicone and silicone co-polymer contact lenses is provided. More particularly, the invention provides an effective ambient temperature storage and disinfecting solution for the disinfection and storage of hydrophilic gel lenses, (HEMA) silicone and silicone co-polymer contact lenses, and gelflex material soft lenses including, for example, the following plastic gel materials: Hydroxyethyl methacrylate (HEMA) or its analogues, ethlene glycol dimethacrylate (EGMA) or its analogues, silicone and silicone co-polymer contact lenses.

In accordance with the present invention, a method for treating a contact lens is provided to kill bacteria that may be associated with the lens which method comprises contacting the lens with an aqueous composition containing trimethoprim and benzyl alcohol present together in an effective concentration for killing bacteria. The method is especially suitable for treating soft, silicone and silicone co-polymer contact lenses. No heat disinfecting is required and therefore, problems associated with elevated temperature treatment are eliminated.

The aqueous composition in accordance with the invention contains trimethoprim and benzyl alcohol present together in an effective amount of concentration for killing bacteria. Generally, an effective concentration of trimethoprim is from about 0.01% and 4.0% by weight of the total composition. Generally, an effective amount of benzyl alcohol which acts as an adjuvant bactericide is from about 0.10% to about 5.0% by weight of the total composition. The combination of trimethoprim and benzyl alcohol provides an ambient temperature disinfecting solution that is effective in killing microorganisms, fungal organisms and viral agents such as herpes simplex. Generally, benzyl alcohol is present in an amount of from about 0.10% and about 5.0% by weight of the total composition. In addition, another important function of benzyl alcohol is to facilitate the dissolution of trimethoprim in the aqueous composition, thereby making it more feasible to utilize trimethoprim.

A salt of ethylenediaminetetraacetic acid may be included as a buffering agent and to provide increased bactericidal properties. Other buffering agents may also be present as hereinafter described.

The remainder of the composition may comprise solely water or may include various alkaline metal and alkaline earth metal water soluble salts to provide an aqueous composition salt content equivalent to about 0.8% to about 1.8% sodium chloride by weight of the total aqueous composition. A humectant such as propylene glycol may be optionally included in the composition.

DETAILED DESCRIPTION OF THE INVENTION

The aqueous ambient temperature disinfecting compositions for soft, silicone and silicone co-polymer contact lenses of the present invention contain trimethoprim and benzyl alcohol. The compositions in accordance with the invention act as a disinfectant for contact lenses without the necessity for heat disinfecting. The compositions are particularly useful for disinfecting soft, silicone and silicone co-polymer contact lenses, and can also be used with hard lenses. As used herein, the term "disinfectant" means a substance that destroys or kills bacteria, fungi, yeasts or viruses.

Trimethoprim and benzyl alcohol are present together in the composition in a concentration sufficient to provide a disinfectant solution for soft contact lenses. Generally, an amount of trimethoprim of from about 0.01% to about 4.0% by weight of the total composition and an amount of benzyl alcohol of from about 0.10% to about 5.0% by weight of the total composition are sufficient concentrations to provide a disinfectant solution for soft contact lenses. Trimethoprim is also known as 2,4-Diamino-5-(3,4,5-trimethoxybenzyl)-pyrimidine and as Syraprim. See, for example, *The Merck Index*, tenth edition, page 1387. Preferably, trimethoprim is present in an amount of about 0.125% by weight of the total composition and benzyl alcohol is present in an amount of about 2.0% by weight of the total composition.

In order to further enhance the disinfectant properties of the composition in accordance with the present invention, ethylenediaminetetiacetic acid (EDTA) or a water soluble salt of ethylenediaminetetraacetic acid that has disinfectant properties is preferably present in an effective amount for enhancing the D value kill factor relating to bacteria, fungus, yeast and/or viral organisms. A preferred salt of EDTA is the disodium salt (disodium edetate). Other salts of EDTA which may be utilized include, for example, mono-, di-, tri- and tetra-alkali metal salts. Generally, an effective amount of EDTA or salt thereof is from about 0.025% to about 0.5% by weight of the total composition. Preferably, disodium edetate is present in an amount of about 0.25% by weight of the total composition.

The compositions of the present invention preferably include at least one essentially neutral water-soluble compatible salt to provide tonicity equivalent to between about 0.8% and 1.8% sodium chloride by weight of the total aqueous composition. Thus, the preferred compsitions according to the invention provide a tonicity which is about the same as or slightly higher than the tonicity of normal human tear fluid. While hypertonic solutions can be desirable since the solution will have a greater osmotic pressure than that of the tear fluid of the contact lens wearer, any soluble salts or mixtures of salts, compatible with ocular tissue, can be used to provide the desired tonicity. Preferably, sodium chloride, potassium chloride or mixtures thereof, are used to provide the desired tonicity. it is understood, however, that one or more essentially neutral, water-soluble alkali or alkaline earth metal salts can be substituted in whole or in part for the sodium or potassium chloride in the solutions of the invention, when tonicity adjustment is desired. Preferably, sodium chloride and potassium chloride are utilized in weight ratio of from about 2:1 to about 7:3, respectively.

Preferably, a buffer or buffers are present in the composition. Suitable buffers are known in the art and include, for example, buffers such as sodium bicarbonate. The preferred combination of buffers is sodim bicarbonate, sodium phosphate (tribasic), sodium bisulfite and sodium biphosphate, present in amounts to provide and maintain the desired pH.

Propylene glycol may optionally be included in the compositions, generally in an amount of from about 0.2% to about 2.5% by weight of the total aqueous composition and preferably in an amount of about 1.0% by weight of the total aqueous composition. The propylene glycol acts as a humectant, preservative and fungal growth inhibitor.

The balance of the composition is purified water U.S.P.

In accordance with one embodiment of the present invention, a treatment method is provided for killing bacteria associated with contact lenses. A contact lens is treated by storing the lens in an aqueous solution containing trimethoprim and benzyl alcohol present together in an effective concentration for killing bacteria. Any of the solutions in accordance with the invention can be used. The lens is brought into contact with an aqueous composition in accordance with the invention for a period of time sufficient for the composition to kill at least a portion of the bacteria associated with the contact lens. For example, the lens is introduced into a container having a solution in accordance with the invention generally after proper cleaning procedures are followed in an amount sufficient to completely immerse the lens. The container is then closed and the contact lens is allowed to remain in the solution for a time sufficient to disinfect the contact lens. No external source of heat is applied and thus, the lens is stored at ambient temperature. Generally, storing the lens in a solution in accordance with the invention for about six hours will provide sufficient disinfection of the contact lens or bacteria for wearing the lens. Thus, the method is ideal for overnight storage of contact lenses or storage between wearing periods. However, it is anticipated that for some solutions in accordance with the invention, less than six hours of storage will be sufficient.

In accordance with the method of the invention, heating of the solution or lens is not required. Thus, the solutions and method of the present invention allow the lens to be disinfected at ambient temperature, eliminating possibility of deleterious effects that may occur when the lens is heated.

The aqueous composition in accordance with the invention is preferably utilized as part of the total patient regimen for maintaining and treating soft, silicone and silicone co-polymer contact lenses. Thus, an effective cleaning step or steps is an improtant part of any effective soft or firm lens treatment and maintenance regimen. Separate cleaning of the lenses insures that the disinfectant properties of the aqueous solution will not be overwhelmed by gross organic or inorganic deposits and pollutants.

An especially preferred rinsing and cold disinfecting solution is:

| Component | Amount (% by weight) |
|---|---|
| Sodium bicarbonate | 0.100 |
| Sodium phosphate (tribasic) | 0.030 |
| Sodium biphosphate | 0.030 |
| Sodium chloride | 0.790 |
| Potassium chloride | 0.368 |
| Disodium EDTA | 0.250 |
| Trimethoprim | 0.125 |
| Sodium bisulfite | 0.050 |
| Benzyl alcohol | 2.000 |
| Propylene glycol | 1.000 |
| Purified water U.S.P. | Balance |

Whereas the present invention has been described with respect to specific embodiment, it will be understood that various changes and modifications will be suggested to one skilled in the art and it is intended that the invention encompass such changes and modifications as fall within the scope of the appended claims.

I claim:

1. A method of treating a contact lens to kill bacteria associated therewith comprising:
    (a) placing the lens in contact with an aqueous composition, said composition comprising water, trimethoprim and benzyl alcohol present together in an effective amount to kill bacteria; and
    (b) maintaining the lens in contact with said aqueous composition for a time sufficient to kill bacteria.

2. The method as recited in claim 1 wherein the lens is completely immersed in said composition for a period of about six hours.

3. The method as recited in claim 1 wherein the lens is completely immersed in said composition overnight or between wearing periods.

4. The method as recited in claim 1 wherein trimethoprim is present in an amount of from about 0.01% to about 4.0% and benzyl alcohol is present in an amount of from about 0.10% to about 5.0%, by weight of the total aqueous composition.

5. The method as recited in claim 4 wherein the concentration of trimethoprim compound is about 0.125% and the concentration of benzyl alcohol is about 2.0%, by weight of the total aqueous composition.

6. The method as recited in claim 1 wherein said aqueous composition further comprises ethylenediaminetetraacetic acid or a water soluble salt thereof.

7. The method as recited in claim 6 wherein ethylenediaminetetraacetic acid or a water soluble salt thereof is present in an amount of from about 0.025% and 0.5% by weight of the total aqueous composition.

8. An aqueous composition for ambient temperature disinfection of soft contact lenses comprising trimethoprim and benzyl alcohol present together in an effective amount to kill bacteria, said composition being compatible with soft contact lenses.

9. The composition of claim 9 wherein trimethoprim is present in an amount of from about 0.01% to about 4.0% and benzyl alcohol is present in an amount of from about 0.1% to about 5.0%, by weight of the total composition.

10. The composition of claim 8 further comprising ethylenediaminetetraacetic acid or a water soluble salt thereof.

11. The composition of claim 10 wherein disodium edetate is present in an amount of from about 0.025% to about 0.5% by weight of the total composition.

12. The composition of claim 10 wherein disodium edetate is present in an amount of about 0.25% by weight of the total composition.

13. The composition of claim 8 wherein the composition has a tonicity of from about 0.8 to about 1.8.

14. The composition of claim 8 further comprising at least one buffering compound.

15. The composition of claim 12 wherein said at least one buffering compound is selected from the group consisting of sodium bicarbonate, sodium phosphate, sodium bisulfite and sodium biphosphate.

16. The composition of claim 14 wherein the composition contains, by weight of the total composition, about 0.125% trimethoprim, about 2.0% benzyl alcohol, about 0.25% of the disodium salt of ethylenediaminetetraacetic acid, about 0.10% sodium bicarbonate, about 0.03% sodium phosphate, about 0.03% sodium biphosphate, about 0.79% sodium chloride, about 0.368% potassium chloride, about 0.05% sodium bisulfite and about 1.0% propylene glycol.

* * * * *

UNITED STATES PATENT AND TRADEMARK OFFICE
CERTIFICATE OF CORRECTION

PATENT NO. : 4,551,461
DATED : November 5, 1985
INVENTOR(S) : Guy J. Sherman

It is certified that error appears in the above-identified patent and that said Letters Patent is hereby corrected as shown below:

Column 2, line 41, delete "arisn" and insert --arisen--.

Column 2, line 59, delete "ethlene" and insert --ethylene--.

Column 4, line 18, delete "compsitions" and insert --compositions--.

Column 4, line 27, delete "it" and insert --It--.

Column 4, line 38, delete "sodim" and insert --sodium--.

Column 5, line 21, delete "improtant" and insert --important--.

Column 5, line 45, delete "embodiment" and insert --embodiments--.

Signed and Sealed this

Twentieth Day of May 1986

[SEAL]

Attest:

DONALD J. QUIGG

Attesting Officer

Commissioner of Patents and Trademarks